(12) United States Patent
Orten

(10) Patent No.: US 6,512,830 B1
(45) Date of Patent: *Jan. 28, 2003

(54) AUSCULTATION APPARATUS

(75) Inventor: Birger Orten, Alesund (NO)

(73) Assignee: Meditron AS, Asker (NO)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/875,965

(22) PCT Filed: Feb. 8, 1996

(86) PCT No.: PCT/NO96/00030

§ 371 (c)(1),
(2), (4) Date: Sep. 11, 1997

(87) PCT Pub. No.: WO96/24287

PCT Pub. Date: Aug. 15, 1996

(30) Foreign Application Priority Data

Feb. 9, 1995 (NO) ............................................. 950495

(51) Int. Cl.[7] .............................. A61B 7/04; A61B 5/02
(52) U.S. Cl. ...................................... 381/67; 600/528
(58) Field of Search ........................... 381/67; 128/559; 600/523, 520; 181/131

(56) References Cited

U.S. PATENT DOCUMENTS

| 3,762,397 | A | | 10/1973 | Cage | |
|---|---|---|---|---|---|
| 4,594,731 | A | | 6/1986 | Lewkowicz | |
| 4,720,866 | A | * | 1/1988 | Elias et al. | 381/67 |
| 4,731,849 | A | * | 3/1988 | Bloomfield, III | 381/67 |
| 5,557,681 | A | * | 9/1996 | Thomasson | 381/67 |
| 5,602,924 | A | * | 2/1997 | Durand et al. | 381/67 |
| 6,026,170 | A | * | 2/2000 | Dieken et al. | 381/67 |

FOREIGN PATENT DOCUMENTS

| DE | 2911056 | | 9/1980 | A61B/5/04 |
|---|---|---|---|---|
| DE | 400607 A | * | 7/1992 | |
| DE | 4100607 | | 7/1992 | A61B/7/04 |

* cited by examiner

Primary Examiner—Forester W. Isen
Assistant Examiner—Brian Tyrone Pendleton
(74) Attorney, Agent, or Firm—Ladas & Parry

(57) ABSTRACT

An electronic stethoscope including a microphone, amplifying equipment, and a loudspeaker for the user, also comprises an adjustable filter circuit. The filter circuit has a bandpass effect, and the center frequency and bandwidth of the passband can be adjusted at will throughout the audible range by the user.

10 Claims, 3 Drawing Sheets

AUSCULTATION APPARATUS

Figure 1:
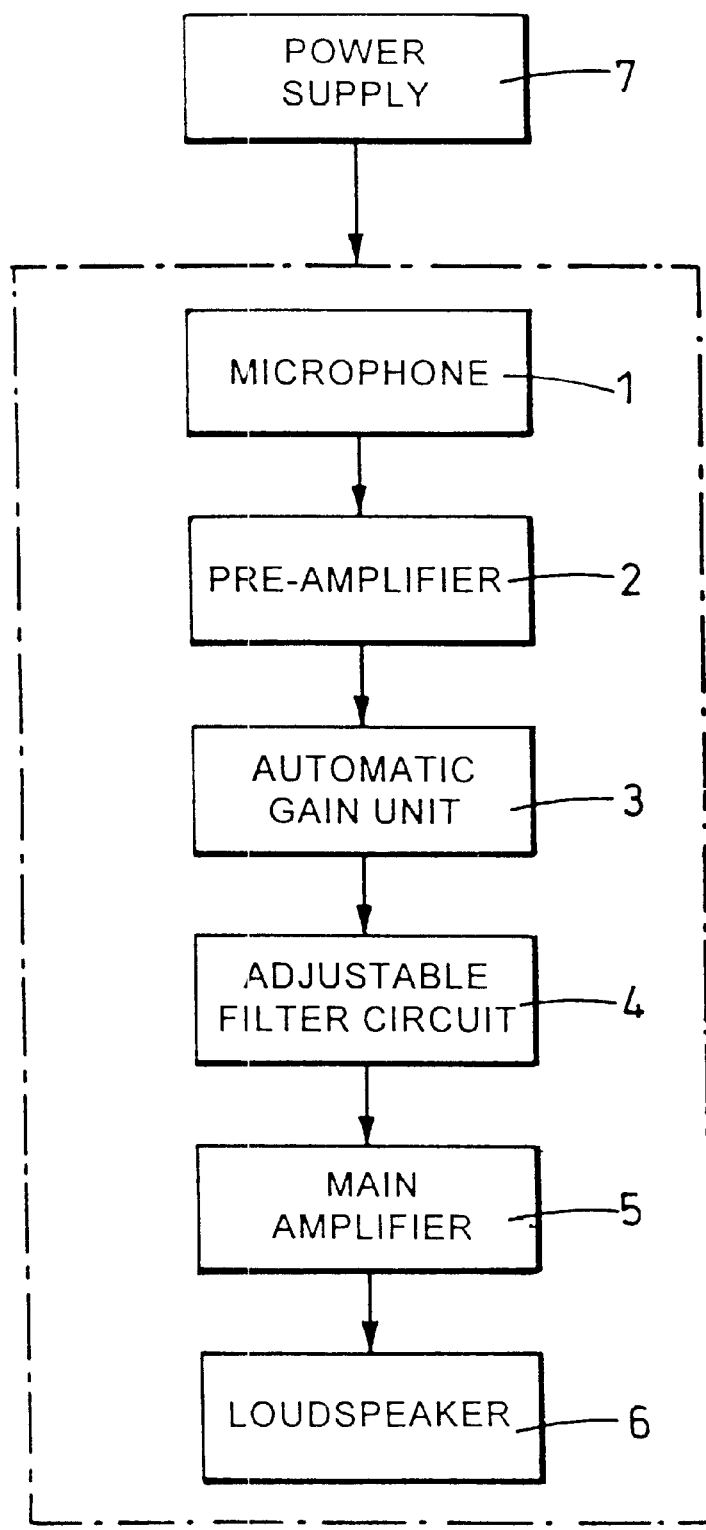

The present invention relates to an ascultation apparatus, i.e. an apparatus for listening to sounds from the internal organs of a living body, preferably the heart, respiratory or circulatory organs of a human, in particular to be able to analyse the sound in a more detailed manner for diagnostic purposes. The apparatus is intended to increase the possibilities for correct diagnosis for e.g. a doctor, by providing more detailed and specific sound information than what is possible when using e.g. an ordinary stethoscope, and the apparatus also provides options for recording, processing and displaying different characteristics of the captured sound.

Various types of "electronic stethoscopes" are previously known: From international No. WO 87/00145 (=SE 452, 946) is known a means for monitoring respiration of infants, with microphones attached to the neck of the child. Each microphone is followed by a preamplifier, a bandpass filter and further amplifying and signal processing equipment. However, a real loudspeaker device for listening to the sound is not included, instead there are various types of warning equipment for giving a signal if a certain type of sound does not appear for a certain period of time. The function of the bandpass filter is to remove irrelevant frequencies, and the relevant and permanently set pass range is 300–1000 Hz when respiratory sounds from a small child are monitored. Thus, this previously known device is specially designed for one signal function, and it cannot be used in the type of comprehensive analysis which is the goal of the present invention.

From U.S. Pat. No. 4,220,160 is known an electronic stethoscope including a microphone and amplifying and processing equipment which lead to a loudspeaker for listening to processed sounds, as well as to other recording equipment. This is a system for transposing or converting the sound in such a manner that e.g. very low frequencies (25–75 Hz) are shifted to frequencies above 250 Hz, which frequencies are more easily audible and also easier to transmit e.g. by telephone. An adjustable highpass filter is inserted right after a microphone preamplifier, in order to remove the very lowest frequencies (adjustable limiting frequency in the range 0,5–20 Hz). Thus, the sound frequencies reproduced in this case are shifted, and must be re-interpreted by the listener.

From U.S. Pat. No. 4,731,849 is known an electronic stethoscope having a microphone, a preamplifier, automatic gain control and bandpass filtering before end amplification to a head set/loudspeaker. In this case the bandpass filter section comprises ten parallel bandpass filters, however, all these filters operate simultaneously to transmit ten selected/pre-set frequency ranges with about the same bandwidth. The output from each filter can be attenuated to zero according to wish, so that one has available ten fixed, selectable ranges which can be used separately or in combination. Thus, this arrangement provides certain options regarding choice of listening range, but is nevertheless a restricted system in this regard. The bandwidth is permanent for each respective one of the filters.

About the same options for varying the listening frequency range is provided in German Offenlegungsschrift DE 41 00 607, which publication also exhibits an electronic stethoscope having various filters which can be switched in and have different filter characteristics, inter alia bandpass characteristics.

However, none of the previously known devices seem to give to the doctor who shall prepare the diagnosis, complete and free options for selecting which frequency range shall be used, i.e. possibilities for deciding freely and immediately which part of the sound spectrum should form the basis of the analysis, without regard to whether the sound shall be listened to or recorded in some other manner.

The present invention has been conceived just to provide such possibilities, and this is achieved in accordance with the invention by providing an apparatus of the type as defined in patent claim 1.

Further embodiments of the invention are defined in the attached dependent patent claims.

Figure 2:
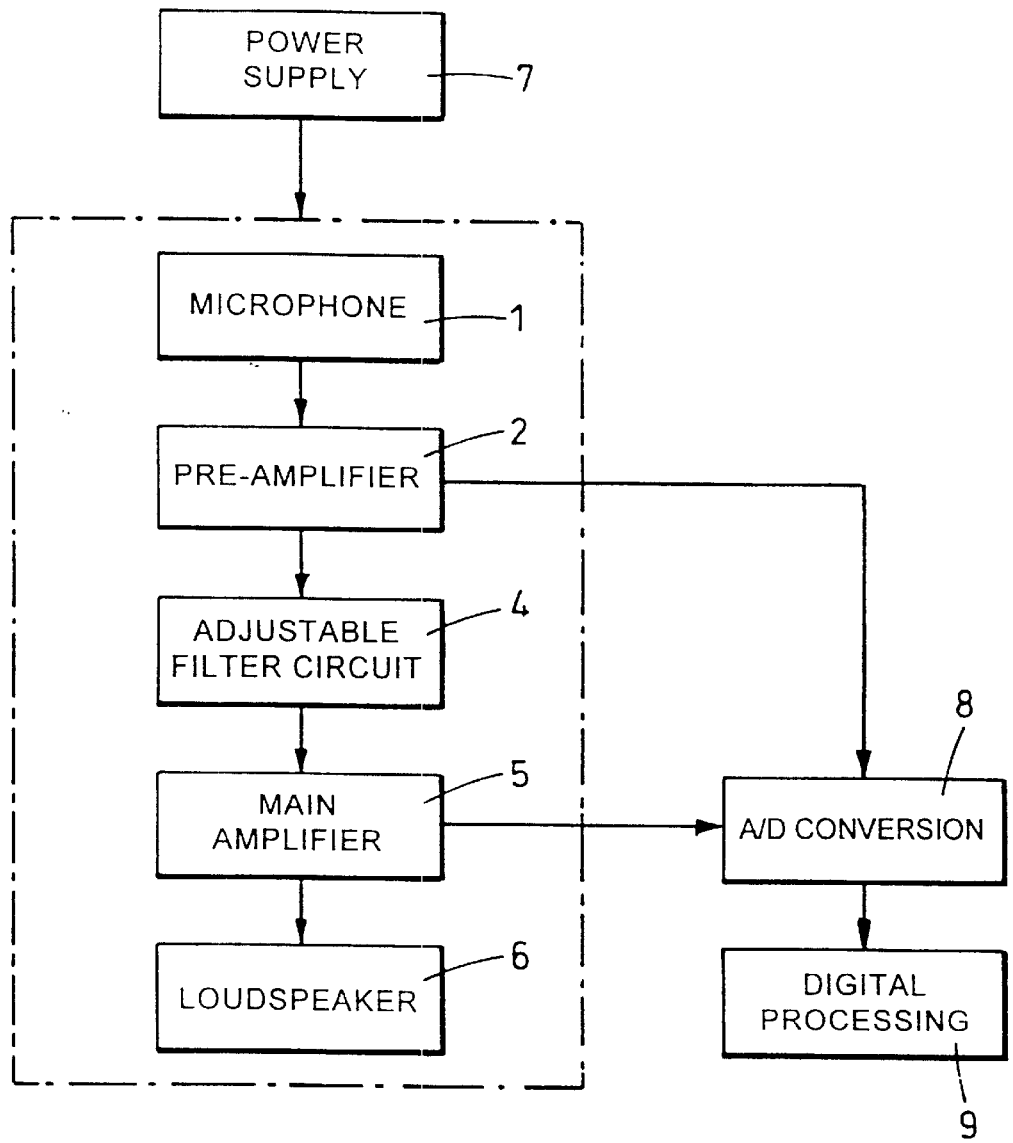
Figure 3:
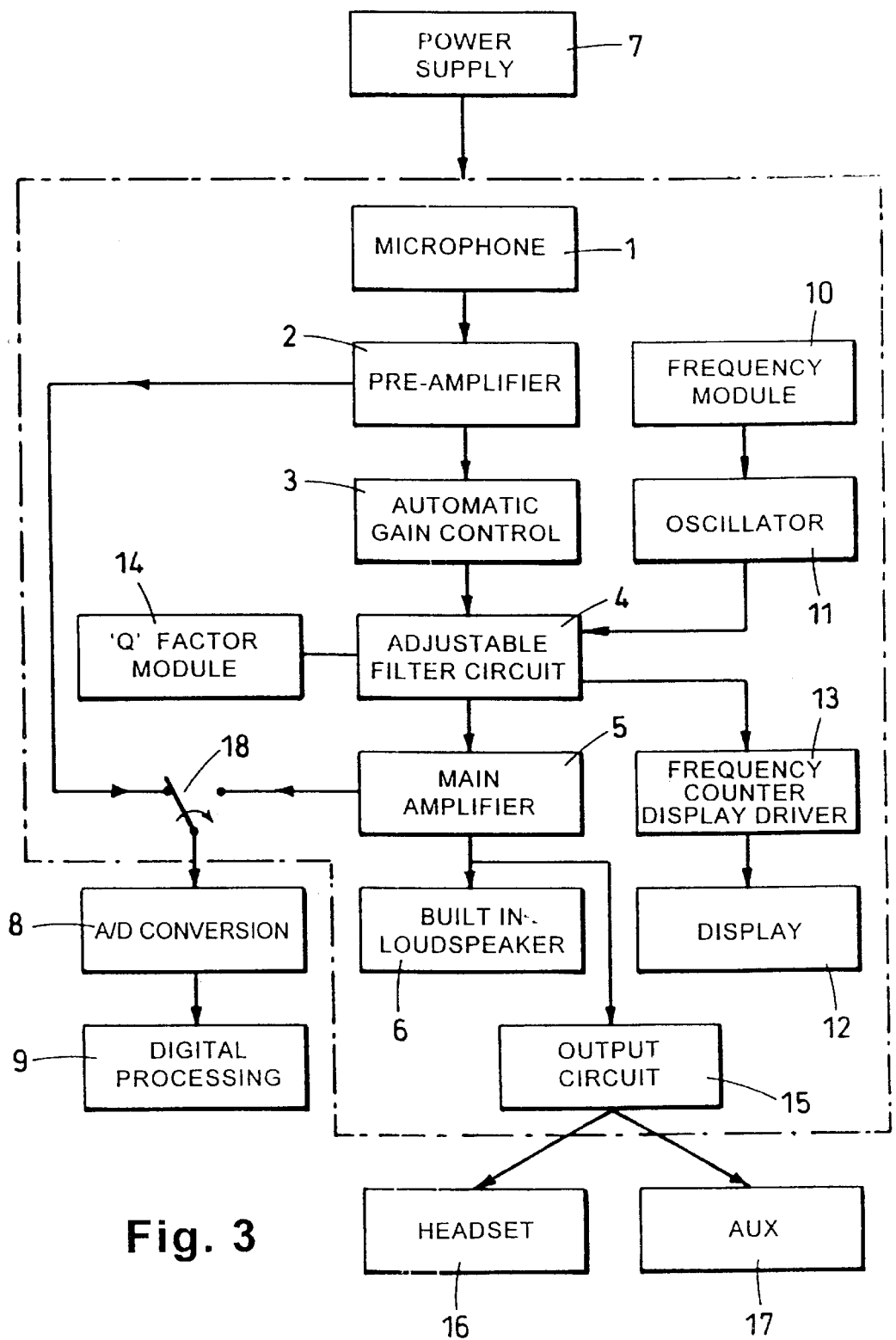

The invention will be described in closer detail in the following, with illumination of exemplary embodiments and with reference to the appended drawings, where FIG. 1 is a block diagram showing an embodiment of the invention which includes an automatic gain control unit, FIG. 2 shows an embodiment including equipment for digital processing of the sound signals, in the form of a block diagram, and FIG. 3 is a more detailed block diagram showing an exemplary embodiment of the apparatus of the invention.

In FIG. 1 appears in a block diagram a relatively simple version of an apparatus in accordance with the invention. The microphone 1 is of a type which is suited to be attached to an appropriate place on a body, in regard to the type of body sound to be monitored. Various microphone types are of interest, however the microphone type itself does not constitute any part of the present invention. The signals captured by the microphone 1 pass to a microphone preamplifier 2 which either may be built together with a microphone in order to shorten the conductor path between microphone and preamplifier, with regard to the fact that the weak signals are to a large degree exposed to degradation from noise, or the preamplifier 2 can be physically built together with the units following thereafter. In many applications it may be sensible to include an automatic gain control unit 3 after the preamplifier to ensure an uniform level of the sound to be analysed. However, such a unit is not absolutely necessary for the invention.

The central feature of the present invention is to be found in connection with the adjustable filter circuit shown with reference numeral 4. The special characteristics of the filter circuit 4 shall be mentioned later. However, the filter circuit 4 is arranged to transmit a certain frequency band, most often within the audible range 20 Hz–20 kHz, but it may also be of interest to make an analysis in an extended sound frequency range beyond the ordinary 20 kHz limit, and also down in the infrasound range below 20 Hz. This filtered signal passes further on to a sound frequency amplifier 5 which is adapted to deliver power to a loudspeaker 6, or possibly a head set may be more appropriate (see FIG. 3). All units 2–5, or possibly 1–5 if the microphone is of a type which requires a voltage supply, can be fed from a common power supply 7.

FIG. 2 shows an embodiment of the apparatus of the invention, which is somewhat different. The differences existing with regard to FIG. 1, are first that the automatic gain control unit 3 has been left out, which has been previously stated as a possibility, and next that an equipment 8 for analog/digital conversion of the signals from the preamplifier has been added, possibly for conversion of signals from the main amplifier 5, i.e. after execution of filtering. The sampled and digitized signal delivered by the converter 8 is passed to a digital processing equipment 9, and it is of course possible to include herein digital filters which are able to conduct the same type of filtering as basically executed in circuit 4. For the rest, the circuit is of the same type as shown in FIG. 1.

FIG. 3 shows, still in the form of a block diagram, a more detailed representation of a circuit which is a combination of the versions shown in FIG. 1 and FIG. 2. Both the automatic gain control unit 3 and the digital equipment 8, 9 are included, and in addition an output circuit 15 has been included, which output circuit is able to deliver a signal to a head set 16 or to auxiliary equipment 17 (a printer, a screen display apparatus or similar) which corresponds to the signal to loudspeaker 6. In order to switch at will concerning digitizing the original signal from preamplifier 2, or digitizing the filtered signal from the main amplifier 5, a switch 18 has been inserted. However, the most important features in the drawing are the units in close association with the adjustable filter circuit 4:

The filter circuit 4 is a bandpass filter wherein both center frequency and bandwidth for the passband shall be adjustable, freely and as desired. A Q factor module 14 takes care of the bandwidth, and this module may be of a type having permanent Q factor values to be selected by means of a switch, or this Q factor module may be of a type having an infinitely variable regulator function, so that any bandwidth can be chosen. The adjustable filter circuit 4 is of a type where the passband center frequency can be adjusted by means of a supplied external frequency. This frequency is supplied from an oscillator 11, and the oscillator frequency is governed by means of a frequency module 10 which sets a number of main frequencies for the oscillator 11. Further variation of the oscillator frequency is achieved by means of an infinitely variable adjustment of a potentiometer (not shown) connected to the oscillator 11.

It will be favourable if the doctor is able to see both the center frequency and the bandwidth used for the moment, and it will therefore be favourable to arrange a display 12 in connection with the filter circuit 4. The display 12 is run by a unit 13 which controls the frequency and drives the display.

Thus, the advantage of the apparatus in accordance with the invention is that the user himself is able to decide exactly which frequencies within the audible picture he desires to listen to by adjusting the center frequency and bandwidth of the bandpass filter. In combination with amplification of the signal from the microphone before and after filtering, it is achieved that it is possible for the user to obtain a sound picture from the loudspeaker which is very rich in detail and very good. It is to be noted that the technology of adjusting frequency and retrieving a certain frequency band for investigating this band separately, in itself is no novelty, since a similar technique has been used previously e.g. within the field of radio technology. But when used in an auscultation apparatus, it is a novelty that the user, e.g. the doctor, has complete control over what part of the audible spectrum can be used in the analysis/diagnosis.

In this connection it is to be understood that a typical sound frequency range for the so called first and second heart sounds is in the range 20–150 Hz, while respiratory sounds are in the range 200–750 Hz, mitral/aortic blood regurgitation is heard in the range 170–900 Hz, mitral stenosis can be heard in the range 25–80 Hz, etc. Thus, when listening for a certain phenomenon, it will be very favourable to be able to remove irrelevant frequencies, and it is clear that the present invention provides new such possibilites.

What is claimed is:

1. Auscultation apparatus, comprising a microphone for direct contact with a body surface, an adjustable electronic bandpass filter circuit connected after the microphone, said filter circuit having a passband center frequency that can be adjusted by means of an externally supplied frequency, and listening/monitoring equipment including a sound frequency amplifier and loudspeaker means for reproduction of the filtered sound, wherein the center frequency as well as bandwidth of the filter passband are independently adjustable where an adjustment of either does not affect the other at least throughout a frequency range of from 20 Hz to 20000 Hz by means of a Q-factor module for controlling bandwidth and a frequency module and an oscillator for the controlling center frequency, said oscillator and said Q-factor module being connected directly and mutually independently to said filter circuit.

2. Auscultation apparatus in accordance with claim 1, wherein the self-contained microphone unit further includes an automatic gain control unit connected to the preamplifier for variable amplification of the signal from the microphone.

3. Auscultation apparatus in accordance with claim 1, or 2, wherein frequency ranges are fixed and center frequency and bandwidth are freely adjustable within each respective range.

4. Auscultation apparatus in accordance with claim 1, or 2, including a quick selector switch for easy selection of bandpass ranges with pre-adjusted center frequencies and Q factors.

5. Auscultation apparatus in accordance with claim 1 or 2, including an infinitely variable regulator connected to the bandpass filter for adjusting Q factor and hence the bandwidth of the passband.

6. Auscultation apparatus in accordance with claim 1 or 2, wherein the bandpass filter includes a display for showing set values of center frequency and bandwidth.

7. Auscultation apparatus in accordance with claim 1 or 2, including a digitizing means for digitizing the signals from the microphone for digital processing.

8. Auscultation apparatus in accordance with claim 1, further comprising a memory means for recording and storing the filtered sound.

9. Auscultation apparatus in accordance with claim 2, further comprising a listening/monitoring equipment comprising a sound frequency amplifier and loudspeaker means for reproduction of the filtered sound.

10. Auscultation apparatus in accordance with claim 2, further comprising a processing means for extracting predefined characteristics of the filtered sound.

* * * * *